United States Patent [19]

Yesair

[11] Patent Number: 5,716,814
[45] Date of Patent: Feb. 10, 1998

[54] METHODS FOR MAKING LYSOPHOSPHATIDYLCHOLINE

[75] Inventor: David W. Yesair, Byfield, Mass.

[73] Assignee: BioMolecular Products, Inc., Byfield, Mass.

[21] Appl. No.: 597,450

[22] Filed: Feb. 2, 1996

[51] Int. Cl.⁶ .................. C12P 13/00; C12P 9/00; C12P 7/64

[52] U.S. Cl. .......... 435/134; 435/128; 435/131; 435/198; 514/724

[58] Field of Search .............. 435/134, 128, 435/131, 198; 514/724

[56] References Cited

U.S. PATENT DOCUMENTS

| | | | |
|---|---|---|---|
| 4,849,132 | 7/1989 | Fujita et al. | 252/356 |
| 5,153,125 | 10/1992 | Kobayashi | 435/128 |
| 5,314,706 | 5/1994 | Colarow et al. | 426/605 |
| 5,538,874 | 7/1996 | Hattori et al. | 435/128 |

FOREIGN PATENT DOCUMENTS 1215868  12/1970  United Kingdom.

OTHER PUBLICATIONS

Hughes, A., The Action of Snake Venoms on Surface Films, Biochem. J. 29:437–444 (1935).

Hanahan, D.J., The Enzymatic Degradation of Phosphatidyl Choline in Diethyl Ether; J. Biol. Chem. 195:199–206 (1952).

Dawson, R.M.C., On the Mechanism of Action of Phospholipase A. Biochem. J. 88:414–423 (1963).

Lecitase, Product Sheet, Novo Nordisk (1990).

Small, D.M., A Classification of Biologic Lipids Based Upon Their Interaction in Aqueous Systems, The Journal of the American Oil Chemist's Society, vol. 45, pp. 108–119 (1968).

Primary Examiner—Leon B. Lankford, Jr.
Assistant Examiner—Christopher R. Tate
Attorney, Agent, or Firm—Wolf, Greenfield & Sacks, P.C.

[57] ABSTRACT

Methods for making lysophosphatidylcholine are provided, comprising hydrolysis of a mixture of phosphatidylcholine and an agent with phospholipase $A_2$. Also disclosed are methods for making a lipid matrix of lysophosphatidylcholine, monoglyceride and fatty acid.

28 Claims, No Drawings

METHODS FOR MAKING LYSOPHOSPHATIDYLCHOLINE

FIELD OF THE INVENTION

This invention relates generally to the field of phospholipid hydrolysis. In particular, this invention relates to an improved method of phospholipase $A_2$ hydrolysis of phosphatidylcholine to produce lysophosphatidylcholine. This invention also relates to a method of making a lipid matrix comprising lysophosphatidylcholine, monoglyceride, and fatty acid.

BACKGROUND OF THE INVENTION

Enzymatic conversion of phosphatidylcholine to lysophosphatidylcholine has been known since the early 1900's. Early investigations of the degradation of lecithin (phosphatidylcholine) by snake venom extracts demonstrated that the action of snake venom hemolysis is upon the lecithin portion of the cell membrane. In 1935, Hughes demonstrated that the hydrolysis of a unimolecular film of lecithin to lysolecithin (lysophosphatidylcholine) is dependent on factors such as pH, temperature and the surface concentration of the lecithin molecules. Packing of the lecithin molecules in the unimolecular layer greatly decreased the rate of hydrolysis. Hanahan demonstrated that an ether-soluble complex between egg phosphatidylcholine and phospholipase $A_2$ resulted in the release of unsaturated fatty acid and lysophosphatidylcholine. Hydrolysis of phosphatidylcholine by phospholipase $A_2$ could not be detected when 95% ethyl alcohol, chloroform or petroleum ether were used as solvents. Experiments performed by Dawson, reported in 1963, also found that phospholipase $A_2$ hydrolyzed phosphatidylcholine to lysophosphatidylcholine and a single fatty acid molecule. Dawson determined that the enzymatic activity was dependent on the presence of calcium ions, and that the addition of ether or butanol stimulated the phospholipase $A_2$ activity. British patent 1,215,868 to Unilever Ltd. described a further modification of the hydrolysis of phospholipid by phospholipase $A_2$, conducting the reaction in the presence of fat (oils).

The processes of phosphatidylcholine hydrolysis disclosed in the prior art suffer from several shortcomings, including incomplete hydrolysis and production of unwanted side products in the hydrolysis reaction. The deficiencies of the prior art methods are severe because the presence of unreacted starting materials or unwanted side products represent an unacceptable level of contaminants in the final reaction product. These unwanted constituents must be removed from the reaction product in order to obtain the desired product, lysophosphatidylcholine, thus necessitating additional purification steps.

The prior art methods described above produce a maximal yield of lysophosphatidylcholine of approximately 70% of the starting phosphatidylcholine. Dawson showed that the addition of ether was required to stimulate the phospholipase $A_2$ activity in the hydrolysis of phosphatidylcholine to the maximum yield of about 60–70%. The maximum yield of lysophosphatidylcholine was obtained when 8% diethyl ether (vol./vol.) in aqueous buffer was the reaction medium; using this reaction medium a two-phase system was observed. Dawson also found that 6% butanol (vol./vol.) could substitute for diethyl ether in the reaction medium to enhance yield of lysophosphatidylcholine, but ethanol and methylisobutylhexane were ineffective for increasing hydrolysis of phosphatidylcholine. Dawson concluded that the stimulatory effect of ether (or butanol) on hydrolysis of phosphatidylcholine was probably due to surface dilution of the closely packed phosphatidylcholine molecules oriented at the lipid interface and a removal of inhibitory fatty acid carbonyl groups from the interface. This conclusion was supported by evidence that addition of fatty acids inhibited the enzymatic hydrolysis of phosphatidylcholine (Dawson). Inhibition of the reaction by added fatty acid resulted either from inhibiting the removal of the fatty acid from the interface, or from formation of a calcium ion—fatty acid thelate, i.e., removal of $Ca^{2+}$ ions required for phospholipase $A_2$ activity. Dawson believed that the removal of calcium ions was the more likely explanation because the further addition of ether to form two phases and solubilize the additional fatty acid did not promote hydrolysis of phosphatidylcholine, whereas increasing the calcium concentration ten fold did partially relieve the inhibition. It was also shown that the phospholipase $A_2$ enzyme purified from cobra venom was dependent on the presence of calcium ions for hydrolysis activity. The requirement for calcium ions in the hydrolysis reaction by phospholipase $A_2$ and the association of calcium ions with fatty acids released by the hydrolysis of phosphatidylcholine is well known in the art (Novo Nordisk).

The present inventor has previously invented methods for the preparation of mixed lipid particles useful in the delivery of drugs and for providing readily absorbable calories to an individual (U.S. Pat. Nos. 4,874,795 and 5,314,921). These methods involve the mixing of lysophosphatidylcholine, monoglyceride and fatty acid in specific molar ratios. Although easily performed, these previous methods use costly, isolated, highly purified lysophosphatidylcholine, thus adding to the expense of the final mixed lipid particle product.

Because of the deficiencies of the prior art noted above, at the present time there is a need for methods by which phosphatidylcholine is more efficiently converted to lysophosphatidylcholine. Such a process would result in more efficient use of phosphatidylcholine and yield fewer unwanted side products and contaminants of the final reaction product. The use of a method in which the end products are in a more pure form would result in substantial cost savings and time saving due to a reduced need for the purification of the end products. There is also a need for a simplified method of producing mixed lipid particles comprising lysophosphatidylcholine, monoglyceride and fatty acid. A method which utilizes phosphatidylcholine as a starting material would reduce the need for the use of a purified lysophosphatidylcholine as a starting material, thus reducing the overall costs for the final mixed lipid particle product.

SUMMARY OF THE INVENTION

The invention provides improved methods for making lysophosphatidylcholine. It also provides improved methods for making compositions containing lysophosphatidylcholine, monoglyceride and fatty acid.

According to one aspect of the invention, a method for making lysophosphatidylcholine is provided. An aqueous mixture of phosphatidylcholine and an agent is contacted with phospholipase $A_2$. In preferred embodiments, the agent is monoglyceride. In other embodiments, the agent may be diglyceride, polyglycerol fatty acid ester, sucrose fatty acid ester, sorbitan fatty acid ester or glycerol. The reaction preferably is performed in the presence of calcium ions.

According to another aspect of the invention, the aqueous mixture of phosphatidylcholine and an agent further contains an organic solvent. In preferred embodiments, the organic solvent is tertiary butyl alcohol. In additional embodiments, the organic solvent may be diethyl ether, a mixture of diethyl ether and ethanol, preferably in which the ethanol represents about 4% of the total organic solvent, a mixture of tertiary butyl alcohol and ethanol, preferably in which the ethanol represents about 4% of the total organic solvent, or methyl isobutyl ketone.

It is an object of the invention to provide a method for making lysophosphatidylcholine which is more efficient than prior art methods. For example, prior art methods of making lysophosphatidylcholine typically achieve no better than 60–70% efficient conversion of phosphatidylcholine starting material. The present invention provides in preferred embodiments a method whereby phosphatidylcholine may be converted to lysophosphatidylcholine with nearly 100% efficiency. Further, the hydrolysis of phosphatidylcholine according to the present invention results in production of small quantities, if any, of unwanted side products. The present invention provides a method which reduces the cost of making lysophosphatidylcholine by converting phosphatidylcholine with nearly 100% efficiency.

According to yet another aspect of the invention, the amount of phosphatidylcholine in the mixture is limited to less than about 40% by weight of the total reaction components. In a preferred embodiment, the amount of phosphatidylcholine in the mixture is about 30% by weight of the mixture.

Although not wishing to be bound by any theory of the invention, it is believed that, according to the methods of the invention, the lamellar structure of phosphatidylcholine/lysophosphatidylcholine/water as described by Small (J. Am. Oil Chemists' Soc., 45:108–119, 1968) is maintained during the sequential enzymatic hydrolysis of phosphatidylcholine/agent/water to lysophosphatidylcholine/agent/fatty acid/water. By providing a set of reaction conditions under which the lamellar structure is maintained, the efficiency of the hydrolysis reaction is enhanced because phosphatidylcholine molecules remain accessible to the phospholipase $A_2$ enzyme throughout the course of the reaction.

The invention also provides methods for separating the formed lysophosphatidylcholine from components of the reaction mixture, such as agents added to enhance hydrolysis of phosphatidylcholine by phospholipase $A_2$, and from byproducts of the hydrolysis reaction, such as fatty acids cleaved from phosphatidylcholine by the action of phospholipase $A_2$. The invention provides a method for separation of lysophosphatidylcholine from all of the aforementioned components, such that the resulting substantially pure product may be used without further purification. In one embodiment, lysophosphatidylcholine is separated from monoglyceride and fatty acid by extraction with acetone.

While virtually any amount of the preferred agent, monoglyceride, will enhance hydrolysis of phosphatidylcholine by phospholipase $A_2$, according to the invention it is preferred that the molar ratio of phosphatidylcholine:monoglyceride is from about 1:1 to about 1:4. Most preferably, the molar ratio of phosphatidylcholine to monoglyceride is about 1:2. According to these embodiments of the invention, hydrolysis of phosphatidylcholine proceeds with nearly 100% efficiency.

Virtually any monoglyceride is useful for enhancing the hydrolysis of phosphatidylcholine by phospholipase $A_2$. However, according to preferred embodiments, the monoglyceride useful in the invention may have an acyl group consisting of anywhere between 8 and 22 carbon atoms. It is preferred that the acyl group of the monoglyceride has between 1 and 4 unsaturations, i.e., double carbon-carbon bonds. Thus, it is preferred that the monoglyceride in the mixture comprises an acyl group selected from the group consisting of an acyl group having one unsaturation, an acyl group having two unsaturations, an acyl group having three unsaturations and an acyl group having four unsaturations. Most preferably, more than 50% of the monoglyceride in the mixture comprises an acyl group selected from the aforementioned group of acyl groups having one, two, three or four unsaturations. Thus, according to the invention, specific monoglycerides may be selected based on the ability of the monoglyceride molecules to separate the phosphatidylcholine molecules for efficient hydrolysis of phosphatidylcholine, and further based on the length and unsaturation of the acyl group which may be desired in useful end products of the reaction, such as lipid matrix compositions described below.

According to another aspect of the invention, methods for making a lipid matrix composition containing lysophosphatidylcholine, monoglyceride and fatty acid are provided. Phosphatidylcholine and monoglyceride are contacted with the phospholipase $A_2$, and the resultant lipid matrix is separated by the removal of water. If desired, monoglyceride and/or fatty acid may be added to the lipid matrix to obtain a preferred molar ratio of the lipid matrix components. According to a preferred embodiment, the lipid matrix may have a molar ratio of lysophosphatidylcholine:the sum of monoglyceride and fatty acid of between about 1:4 and 1:12. More preferably, the molar ratio of lysophosphatidylcholine:the sum of monoglyceride and fatty acid may be between about 1:5 and 1:6. In another preferred embodiment, the constituents of the lipid matrix may be present in a molar ratio of lysophosphatidylcholine:monoglyceride:fatty acid of between 1:4:2 and 1:2:4. Most preferably, the lipid matrix may consist of lysophosphatidylcholine, monoglyceride and fatty acid in a molar ratio of lysophosphatidylcholine:monoglyceride:fatty acid of 1:4:2, 1:3:3 or 1:3:2.

In an additional embodiment, the method of making a lipid matrix containing lysophosphatidylcholine, monoglyceride and fatty acid may include the use of a monoglyceride which is derived from natural triglyceride. Another embodiment of the method of making a lipid matrix composition is contemplated wherein more than 50% of the monoglyceride in the mixture comprises an acyl group selected from the group consisting of an acyl group having one unsaturation, an acyl group having two unsaturations, an acyl group having three unsaturations and an acyl group having four unsaturations.

These and other aspects and objects of the invention will be described in further detail in connection with the Detailed Description of the Invention.

DETAILED DESCRIPTION OF THE INVENTION

The invention is an improved method for making lysophosphatidylcholine which involves contacting phosphatidylcholine and an agent with phospholipase $A_2$. The formed lysophosphatidylcholine optionally may be separated from the added agent and/or the fatty acids which are liberated by the action of phospholipase $A_2$ on phosphatidylcholine. The method enables substantially complete hydrolysis of phosphatidylcholine to lysophosphatidylcholine in a single step. If desired, the agent may be monoglyceride and the resulting lipid matrix of lysophosphatidylcholine, monoglyceride and fatty acids may be separated from the phospholipase $A_2$, trace unreacted phosphatidylcholine, water, organic solvents, and any impurities present in the reaction mixture.

The starting material for the method is phosphatidylcholine, a phospholipid composed of a polar hydrophilic head group of choline, phosphate and glycerol linked to a nonpolar hydrophobic tail group consisting of two fatty acid molecules. Phosphatidylcholine may be obtained with specific fatty acid groups, or with a mixture of various fatty acid groups. For example, Phospholipon® 80 (American Lecithin, Oxford, Conn.), is a mixture of phosphatidylcholine molecules having a variety of fatty acid acyl groups linked to the polar head group.

In the method of the present invention, an agent is added to phosphatidylcholine in the presence of water to make an aqueous mixture, and the mixture is subsequently contacted with phospholipase $A_2$ under conditions which permit hydrolysis of the phosphatidylcholine molecules. It is believed that phosphatidylcholine in aqueous buffer will form a lamellar (bilayer) structure with the polar head groups of phosphatidylcholine oriented to the outside of the bilayer. It further is believed that phosphatidylcholine when mixed with an agent of the invention and heated will form and maintain a similar lamellar structure. The addition of an agent is believed to achieve several purposes. First, the molecules of the agent are believed to separate the phosphatidylcholine molecules to allow greater access to the phosphatidylcholine by phospholipase $A_2$, thus enabling complete hydrolysis to lysophosphatidylcholine. Second, addition of the agent is believed to maintain the lamellar structure during the hydrolysis reaction. Third, addition of the agent is believed to maintain fluidity of the phosphatidylcholine bilayer to enhance hydrolysis by phospholipase $A_2$. Thus, any agent which has one or more of the aforementioned characteristics is believed suitable for adding to phosphatidylcholine to facilitate hydrolysis by phospholipase $A_2$. It is preferable that the agent be selected from amongst the group consisting of monoglyceride, diglyceride, polyglycerol fatty acid ester, sucrose fatty acid ester, sorbitan fatty acid ester and glycerol. Most preferably, the agent is monoglyceride.

Monoglyceride is composed of a glycerol head group to which one fatty acid acyl group is attached. Preferred acyl groups of monoglyceride useful in the invention may range in number of carbon atoms from 8 to 22. Acyl groups of monoglyceride may be saturated or unsaturated, preferably with 1–4 double bonds in the carbon chain. The monoglyceride may be highly purified or may be added in a crude form, depending on the needs of the user and the tolerance for impurities in the reaction mixture. Monoglycerides useful in the invention may represent a mixture of monoglyceride molecules having different size and saturation-state acyl groups, or the monoglyceride may represent only a single type of acyl group, e.g., mono-olein, mono-palmitin. Examples of a mixture of monoglycerides useful in the invention include Dimodan™ LSK and Dimodan™ OK (Danisco Ingredients USA, Inc., New Century, Kans.).

Diglyceride molecules are also useful in the method of the invention for enhancing the hydrolysis of phosphatidylcholine by phospholipase $A_2$. A diglyceride molecule consists of a glycerol head group to which two fatty acid acyl groups are attached. As with the acyl group of monoglyceride, the acyl groups of diglyceride preferably have carbon chain links from 8 to 22 carbon atoms and 1 to 4 unsaturations. As with monoglyceride, the specific acyl groups, purity, and mixture of diglyceride molecules useful in the invention depend on the requirements of the individual user. Any combination or type of diglyceride molecules is contemplated by the invention, so long as the hydrolysis of phosphatidylcholine is enhanced.

Other agents such as polyglycerol fatty acid esters, sorbitan fatty acid esters, sucrose fatty acid esters and glycerol may also enhance the hydrolysis of phosphatidylcholine by separation of the phosphatidylcholine molecules and maintenance of a lamellar structure and fluidity. Such compounds are described in U.S. Pat. No. 4,849,132. A polyglycerol fatty acid ester molecule consists of mono-, di- or polyesters of fatty acids with 4–12 polymerized glycerol molecules. A sorbitan fatty acid ester molecule consists on mono-, di- or polyesters of fatty acids with sorbitol, sorbitan and sorbide. A sucrose fatty acid ester molecule consists of mono-, di- or polyesters of fatty acids with sucrose. As with the acyl group of monoglyceride, the fatty acids/acyl groups of polyglycerol fatty acid ester, sorbitan fatty acid ester and sucrose fatty acid ester preferably have carbon chains of 8–22 carbon atoms and 1–4 unsaturations. As above, the specific acyl groups, purity, and mixture of agent molecules useful in the invention depend on the requirements of the individual user.

Any single agent or mixture of different agents which enhances hydrolysis of phosphatidylcholine is contemplated as useful for the invention. The aforementioned agents are available commercially from a variety of sources.

Phosphatidylcholine is hydrolyzed to lysophosphatidylcholine by the action of phospholipase $A_2$, which severs the ester bond linking a fatty acid group to the 2-position of the glycerol in the head group of phosphatidylcholine. Phospholipase $A_2$ may be purified from a variety of sources, or it may be obtained from commercial sources (e.g. Lecitase™ 10 L, Novo Nordisk, Denmark). For full activity, phospholipase $A_2$ is believed to require the presence of $Ca^{2+}$ ions in the reaction mixture. While typically there is a low level of $Ca^{2+}$ ions in the commercial phospholipase $A_2$ preparations such that phospholipase $A_2$ is active, it is preferred that $Ca^{2+}$ ions be added to the reaction mixture for full activity. It should be noted that $Ca^{2+}$ ions are depleted from the reaction mixture by ionic bonding with the acid group of fatty acids liberated during hydrolysis of phosphatidylcholine. Therefore it is preferred that sufficient $Ca^{2+}$ ions are added to the reaction mixture to maintain full activity of phospholipase $A_2$. In this invention, it is most preferable that the user supplement the calcium ion concentration to achieve a molar ratio of calcium ion:phosphatidylcholine of at least 1:1.

It will be recognized by persons of skill in the art that other ions may be substituted for the $Ca^{2+}$ ions in order to maintain full activity of the phospholipase $A_2$ enzyme. While not all ions may substitute for $Ca^{2+}$ ions in this reaction, the specific type and concentration of ions adequate for maintenance of phospholipase $A_2$ activity easily may be tested by one of ordinary skill in the art.

As disclosed above, the method of making lysophosphatidylcholine comprises contacting an aqueous mixture of phosphatidylcholine and an agent with phospholipase $A_2$. It is believed that the aqueous nature of the mixture facilitates the orientation of the polar portions of the phosphatidylcholine molecules such that a lamellar structure is formed. A lamellar structure is believed preferred for efficient hydrolysis of phosphatidylcholine to lysophosphatidylcholine by phospholipase $A_2$. It therefore is contemplated that nonaqueous mixtures of phosphatidylcholine and an agent could also be utilized in the method of the invention, if such nonaqueous mixtures correctly orient the phosphatidylcholine and agent molecules in a lamellar structure, and if the specificity of phospholipase $A_2$ hydrolysis is retained.

Other reaction conditions, such as pH, time and temperature, may be varied to achieve optimal hydrolysis of phosphatidylcholine. For example, phospholipase $A_2$ has a pH optimum of pH 8–9 which should be maintained to retain maximal enzyme activity. During the progress of the reaction, as fatty acids are released by hydrolysis of phosphatidylcholine, the pH of the reaction mixture may change. Such a change of pH may require the addition of base to maintain the optimal range of pH 8–9. Any base which effectively raises the pH to the optimal range without interfering with the hydrolysis of phosphatidylcholine may be used. Applicant has successfully used aqueous sodium hydroxide for this purpose, however other formulations of sodium hydroxide or other bases may be employed for the same purpose. If the particular reaction conditions employed result in an increase in pH, then it is contemplated that acid may be added to maintain optimal pH.

Hydrolysis of phosphatidylcholine by phospholipase $A_2$ will proceed at many temperatures, but it is preferred that the reaction is carried out at the optimal temperature for enzymatic activity (70°–80° C.). Such a temperature is preferred for the reason that the phosphatidylcholine/agent bilayer structure will be fluid yet coherent, allowing for access of the $PLA_2$ to the phosphatidylcholine molecules. Other optimal temperatures may be determined with minimal experimentation by one of ordinary skill in the art depending on the specific reaction mixture employed in the method of the invention.

The time for the reaction may be chosen by the user of the method as is convenient, so long as the hydrolysis of phosphatidylcholine has progressed to an extent desired. It is preferred that the reaction proceed for 1 to 5 days, most preferably for 2 days.

As mentioned above, hydrolysis of phosphatidylcholine is believed most efficient when a lamellar structure is maintained in the reaction mixture. Hence it is preferred that the reaction components be combined in amounts which maintain a lamellar structure throughout the course of the reaction. The amount of phosphatidylcholine to be used in the method of the invention is quantified as a weight percentage of the total reaction mixture. Weight percentage is calculated by dividing the weight of a single reaction component divided by the sum of the weights of all reaction components.

It is preferred that the amount of phosphatidylcholine in the reaction mixture represent not more than about 40% by weight of the total reaction mixture. Reaction mixtures comprising more than about 40% phosphatidylcholine by weight are likely to separate into a non-lamellar two-phase system which does not permit efficient hydrolysis of the phosphatidylcholine. Most preferably, the phosphatidylcholine represents about 30% by weight of the total reaction mixture.

An agent may be added to the mixture at any weight percentage which enhances the hydrolysis of phosphatidylcholine over the amount of hydrolysis of phosphatidylcholine alone by phospholipase $A_2$. Most preferably, the agent is monoglyceride. When present in the reaction mixture, virtually any amount of monoglyceride will enhance the hydrolysis of phosphatidylcholine by phospholipase $A_2$. Preferably the molar ratio of phosphatidylcholine:monoglyceride is 1:0.1–1:10. To reach high yields of lysophosphatidylcholine it is preferred to have a molar ratio of phosphatidylcholine:monoglyceride of about 1:1–1:4. Most preferably, the molar ratio of phosphatidylcholine:monoglyceride is about 1:2.

The desired end products of the reaction of phosphatidylcholine and agent with phospholipase $A_2$ are lysophosphatidylcholine alone, a combination of lysophosphatidylcholine with fatty acid or agent, or lysophosphatidylcholine in combination with fatty acid and agent. In particular, when the agent is monoglyceride, a preferred end product is a lipid matrix comprising phosphatidylcholine, monoglyceride and fatty acid. The utility of this lipid matrix has been disclosed in U.S. Pat. Nos. 4,874,795 and 5,314,921.

Where the end product is a lipid matrix composition of lysophosphatidylcholine, monoglyceride and fatty acid, it is preferred that the constituents of the lipid matrix be present in the molar ratio of lysophosphatidylcholine:the sum of monoglyceride and fatty acid of about 1:3 to 1:12. Most preferably, the molar ratio of lysophosphatidylcholine:the sum of monoglyceride and fatty acid is about 1:5–1:6. It is also preferred that the individual components of the lipid matrix are present in particular molar ratios in relation to one another. Thus, it is preferred that the molar ratios of lysophosphatidylcholine:monoglyceride:fatty acid are 1:4:2–1:2:4. Most preferably, the molar ratios of lysophosphatidylcholine:monoglyceride:fatty acid are either 1:4:2, 1:3:3 or 1:3:2.

Additional monoglycerides and fatty acids may be added to the lysophosphatidylcholine/monoglyceride/fatty acid mixture and melted or mixed to yield compositions of matter as defined in U.S. Pat. No. 4,874,795. Thus, monoglyceride and/or fatty acid may be added to the lipid matrix if it is desired to alter the molar ratios of monoglyceride and/or fatty acid to yield a desired product.

The lipid matrix produced by the method of the invention is useful for, inter alia, delivery of drugs. When so desired, a pharmaceutical composition may be added to the reaction mixture, for inclusion in the lipid matrix, at any time which does not adversely affect the integrity of the pharmaceutical composition. Preferably the desired pharmaceutical composition is added subsequent to the formation of the lipid matrix.

The method of making lysophosphatidylcholine, according to the invention, may also optionally include separation of lysophosphatidylcholine from other reaction components. Thus, lysophosphatidylcholine may be separated from fatty acid, agent (e.g. monoglyceride) or fatty acid and agent. In other embodiments, where a lipid matrix comprising lysophosphatidylcholine, monoglyceride and fatty acid is the desired end product, other reaction components such as phospholipase $A_2$, water, organic solvents and excesses of monoglyceride or fatty acid may be the components which are separated from the lipid matrix.

Many methods known to those of ordinary skill in the art will be applicable to separation of lysophosphatidylcholine from other reaction components based on differential solubilities, molecular weights, molecular sizes or other properties. For example, lysophosphatidylcholine may be separated from other components by preparative silica gel chromatography. Preferably, lysophosphatidylcholine can be separated by extraction of the reaction mixture with acetone. This method relies on the insolubility of phospholipids in acetone; lysophosphatidylcholine precipitates as a solid which is easily recovered from other reaction constituents. Other separation methods will be known to those of ordinary skill in the art.

Compositions containing lysophosphatidylcholine, alone or in combination with monoglyceride and/or fatty acids, are useful as emulsifiers, antioxidants and surfactants in cosmetic and dermatological preparations.

As disclosed above, the methods of the invention also contemplate the removal of water and/or other solvents from the reaction mixture to recover desired end products. Thus, the method of making any of the foregoing products may include the removal of water or solvents as part of, or separate from, the separation processes outline above.

Any method known in the art for the removal of water, aqueous solvents, or mixtures of aqueous and organic solvents may be used so long as the desired end products of the hydrolysis reaction are not adversely affected. It is preferred that methods which are scalable to industrial production of lysophosphatidylcholine or lipid matrix compositions be employed. For example, solvents may be removed from desired end products by heating, lyophilization, or spray drying processes. Such methods may be employed for such a time and to such an extent so as to remove all or part of the water or solvent mixtures as desired by the user. Preferably, reaction products are heated to remove water, thereby yielding a paste of lysophosphatidylcholine or lipid matrix.

EXAMPLE 1

Phosphatidylcholine (Phospholipon® 80, estimated molecule weight 785, American Lecithin, contains approximately 80% phosphatidylcholine) and monoglycerides (Dimodan™ LSK and Dimodan™ OK, estimated molecular weight 356, Danisco Ingredients) are combined at a phosphatidylcholine:monoglyceride molar ratio of 1:1 to 1:4. The preferred ratio of phosphatidylcholine:monoglyceride is 1:2. These components are mixed together and heated at 70°–80° C. to obtain a uniform melt, i.e., absence of any observable schleiren. Sufficient water is then added so that phosphatidylcholine represents 30% by weight of the total reaction components. The reaction components are mixed and heated at the reaction temperature of 70°–80° C. to obtain a uniform colloidal consistency. The pH is adjusted and maintained at approximately pH 8 to pH 9 with aqueous sodium hydroxide. Lecitase™ 10L, a phospholipase $A_2$ enzyme (Novo Nordisk, Denmark), is added at approximately 2 ml per kg of Phospholipon® 80. Further addition of calcium ions is not necessary, presumably due to the calcium ions present in the enzyme preparation. The reaction conditions of temperature, stirring and pH are maintained for 2 days, until the hydrolysis of phosphatidylcholine is complete. After hydrolysis is complete, the water is removed with heat to yield a paste.

Additional monoglyceride and fatty acid optionally is added to the lysophosphatidylcholine/monoglyceride/fatty acid lipid matrix and melted together with mixing according to the above method to yield compositions of matter as defined in U.S. Pat. No. 4,874,975.

To obtain high purity lysophosphatidylcholine, the end products of the reaction are precipitated by acetone, which extracts both the monoglycerides and the fatty acids from the lysophosphatidylcholine/monoglyceride/fatty acid hydrolysis products described above. Upon addition of acetone, lysophosphatidylcholine precipitates out of solution, and may be recovered by any art-standard process.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:

1. A method for making lysophosphatidylcholine comprising:
    combining an agent and phosphatidylcholine with water to form in the water an aqueous dispersion of a mixture of the agent and phosphatidylcholine, and
    contacting the aqueous dispersion of the mixture with phospholipase $A_2$ to form a reaction mixture in which phospholipase $A_2$ converts phosphatidylcholine into lysophosphatidylcholine, wherein the agent is selected from the group consisting of monoglyceride, diglyceride, polyglycerol fatty acid ester, sucrose fatty acid ester, sorbitan fatty acid ester and glycerol recovering lysophosphatidylcholine.

2. The method of claim 1 wherein the aqueous dispersion of the mixture is contacted with phospholipase $A_2$ in the presence of calcium ions.

3. The method of claim 1 wherein the phosphatidylcholine in the mixture is less than about 40% by weight of the mixture.

4. The method of claim 3 wherein the phosphatidylcholine in the mixture is about 30% by weight of the mixture.

5. The method of claim 1, wherein the agent is monoglyceride.

6. The method of claim 5 wherein the monoglyceride has an acyl group and the acyl group has between 8 and 22 carbon atoms.

7. The method of claim 5, further comprising recovering lysophosphatidylcholine formed in the reaction mixture.

8. The method of claim 7, further comprising separating lysophosphatidylcholine from monoglyceride.

9. The method of claim 7, wherein the mixture contains a fatty acid, and further comprising separating lysophosphatidylcholine from fatty acid.

10. The method of claim 7, wherein the mixture contains a fatty acid, further comprising separating lysophosphatidylcholine from monoglyceride and fatty acid.

11. The method of claim 10, wherein separation of lysophosphatidylcholine from monoglyceride and fatty acid comprises extraction with acetone.

12. The method of claim 1, further comprising recovering lysophosphatidylcholine formed in the reaction mixture.

13. The method of claim 12, further comprising separating lysophosphatidylcholine from fatty acid.

14. The method of claim 12, further comprising separating lysophosphatidylcholine from the agent.

15. The method of claim 12, further comprising separating lysophosphatidylcholine from fatty acid and the agent.

16. The method of claim 15, wherein separation of lysophosphatidylcholine from fatty acid and the agent comprises extraction with acetone.

17. A method for making lysophosphatidylcholine comprising:
    combining an agent, phosphatidylcholine, and an organic solvent with water to form in the water an aqueous dispersion, containing a mixture of the agent and phosphatidylcholine, the aqueous dispersion containing the organic solvent wherein the solvent is selected from the group consisting of diethyl ether, tertiary butyl alcohol, diethyl ether/ethanol mixtures, tertiary butyl alcohol/ethanol mixtures, and methyl isobutyl ketone, and
    contacting the aqueous dispersion of the mixture with phospholipase $A_2$ to form a reaction mixture in which phospholipase $A_2$ converts phosphatidylcholine into lysophosphatidylcholine, wherein the agent is selected from the group consisting of monoglyceride, diglyceride, polyglycerol fatty acid ester, sucrose fatty acid ester, sorbitan fatty acid ester, and glycerol recovering lysophosphatidylcholine.

18. A method for making lysophosphatidylcholine comprising:

combining phosphatidylcholine and monoglyceride with water to form in the water an aqueous dispersion of a mixture of phosphatidylcholine and monoglyceride, wherein the ratio of phosphatidylcholine:monoglyceride is from about 1:1 to about 1:4, and contacting the aqueous dispersion of the mixture with phospholipase $A_2$ to form a reaction mixture in which phospholipase $A_2$ converts phosphatidylcholine into lysophosphatidylcholine recovering lysophosphatidylcholine.

19. The method of claim 18 wherein the ratio of phosphatidylcholine:monoglyceride is about 1:2.

20. A method for making a composition containing lysophosphatidylcholine, monoglyceride and fatty acid, comprising:

contacting an aqueous mixture of phosphatidylcholine and monoglyceride with phospholipase $A_2$, and recovering a lipid complex containing lysophosphatidylcholine, monoglyceride and fatty acid, wherein the molar ratio of lysophosphatidylcholine:the sum of monoglyceride and fatty acid in the recovered lipid complex composition is between 1:3 and 1:12.

21. The method of claim 20 wherein the molar ratio of lysophosphatidylcholine:the sum of monoglyceride and fatty acid in the recovered lipid complex composition is between 1:5 and 1:6.

22. The method of claim 21 wherein the recovered lipid complex composition has a lysophosphatidylcholine:monoglyceride:fatty acid molar ratio between 1:4:2 and 1:2:4.

23. The method of claim 22 wherein the recovered lipid complex composition has a lysophosphatidylcholine:monoglyceride:fatty acid molar ratio selected from the group consisting of 1:4:2, 1:3:3 and 1:3:2.

24. The method of claim 20 or 22 wherein the monoglyceride is derived from natural triglyceride.

25. The method of claim 20, wherein the step of recovering the lipid complex comprises removal of water.

26. A method for making lysophosphatidylcholine comprising:

combining an agent and phosphatidylcholine with water to form in the water an aqueous dispersion of a mixture of the agent and phosphatidylcholine, and contacting the aqueous dispersion of the mixture with phospholipase $A_2$ to form a reaction mixture in which phospholipase $A_2$ converts phosphatidylcholine into lysophosphatidylcholine, wherein the agent is present in an amount effective to enhance the conversion of phosphatidylcholine to lysophosphatidylcholine in the reaction mixture compared to the conversion of phosphatidylcholine to lysophosphatidylcholine in the reaction mixture absent the agent, wherein the agent is selected from the group consisting of monoglyceride, diglyceride, polyglycerol fatty acid ester, sucrose fatty acid ester, sorbitan fatty acid ester, and glycerol recovering lysophosphatidylcholine.

27. The method of claim 26, wherein the agent is present in an amount effective to increase to nearly 100% the efficiency of conversion of phosphatidylcholine to lysophosphatidylcholine in the reaction mixture.

28. A method for making lysophosphatidylcholine comprising:

combining an agent and phosphatidylcholine to form a mixture of the agent and phosphatidylcholine, wherein the agent is selected from the group consisting of monoglyceride, diglyceride, polyglycerol fatty acid ester, sucrose fatty acid ester, sorbitan fatty acid ester, and glycerol, combining the mixture with water to form in the water an aqueous dispersion of the mixture, and contacting the aqueous dispersion of the mixture with phospholipase $A_2$ to form a reaction mixture in which phospholipase $A_2$ converts phosphatidylcholine into lysophosphatidylcholine recovering lysophosphatidylcholine.

* * * * *

UNITED STATES PATENT AND TRADEMARK OFFICE

CERTIFICATE OF CORRECTION

PATENT NO. : 5,716,814

DATED : 2/10/98

INVENTOR(S): David W. Yesair

It is certified that errors appear in the above-identified patent and that said Letters Patent is hereby corrected as shown below:

Column 2, line 10, delete "thelate" and insert --chelate--.

Column 6, line 13, delete "consists on" and insert --consists of--.

Column 7, line 27, delete "PLA$_2$" and insert --phospholipase A$_2$--.

Column 7, line 46, delete "divided".

Column 9, line 8, delete "outline" and insert --outlined--.

Column 9, line 34 delete "schleiren" and insert --schlieren--.

Signed and Sealed this

Eleventh Day of August 1998

Attest:

BRUCE LEHMAN

Attesting Officer

Commissioner of Patents and Trademarks